(12) United States Patent
Sekino et al.

(10) Patent No.: US 7,645,245 B2
(45) Date of Patent: Jan. 12, 2010

(54) ENDOSCOPIC LITHOTRIPSY APPARATUS AND LITHOTRIPSY METHOD OF TREATMENT OBJECT USING THE APPARATUS

(75) Inventors: Naomi Sekino, Hachioji (JP); Tsuruo Hatori, Sagamihara (JP); Koji Shimomura, Hachioji (JP); Hiroshi Okabe, Hachioji (JP); Shinji Hatta, Hachioji (JP); Hiroo Ono, Koganei (JP); Tomohisa Sakurai, Sagamihara (JP); Takeaki Nakamura, Hino (JP)

(73) Assignee: Olympus Corporation (JP)

( * ) Notice: Subject to any disclaimer, the term of this patent is extended or adjusted under 35 U.S.C. 154(b) by 1149 days.

(21) Appl. No.: 10/729,074

(22) Filed: Dec. 4, 2003

(65) Prior Publication Data

US 2004/0138594 A1 Jul. 15, 2004

(30) Foreign Application Priority Data

Dec. 4, 2002 (JP) ............................. 2002-352702

(51) Int. Cl.
*A61H 1/00* (2006.01)
(52) U.S. Cl. ................................. 601/4; 601/2; 600/439
(58) Field of Classification Search ................. 606/127, 606/128, 169, 100; 600/436, 2, 439, 562–571; 601/1–4
See application file for complete search history.

(56) References Cited

U.S. PATENT DOCUMENTS 4,660,573 A 4/1987 Brumbach
4,911,147 A 3/1990 Washizuka
4,989,588 A * 2/1991 Kubota et al. ................... 606/2
5,540,702 A * 7/1996 Walz ........................... 606/128
5,722,980 A 3/1998 Schulz et al.
5,836,897 A * 11/1998 Sakurai et al. .................. 601/2
6,036,661 A * 3/2000 Schwarze et al. .............. 601/4
6,149,656 A 11/2000 Walz et al.
2002/0010478 A1* 1/2002 Menne et al. ............... 606/128
2003/0045887 A1* 3/2003 Sakurai et al. ............. 606/128
2004/0010267 A1* 1/2004 Nakamura et al. .......... 606/128

OTHER PUBLICATIONS

Search Report issued by European Patent Office on May 19, 2006 in connection with corresponding European application No. EP 03 02 7819.

* cited by examiner

*Primary Examiner*—Long V Le
*Assistant Examiner*—Sanjay Cattungal
(74) *Attorney, Agent, or Firm*—Ostrolenk Faber LLP

(57) ABSTRACT

An endoscopic lithotripsy probe apparatus includes a probe, ultrasonic-vibration source, mechanical shock generation source, and switch-mechanism. The ultrasonic-vibration source is detachably attached to the probe to transmit an ultrasonic-vibration to the probe in a state in which the proximal end of the probe is connected to the ultrasonic-vibration source. The mechanical shock generation source, which is disposed on the side of the proximal end of the probe, applies a force to the ultrasonic-vibration source in a state in which the ultrasonic-vibration source is detached from the proximal end of the probe, and allows the ultrasonic-vibration source to collide with the proximal end of the probe so that a mechanical shock is applied to the probe. The switch-mechanism switches a state in which the ultrasonic-vibration from the ultrasonic-vibration source is transmitted to the probe and a state in which the mechanical shock from the mechanical shock generation source is transmitted.

33 Claims, 5 Drawing Sheets

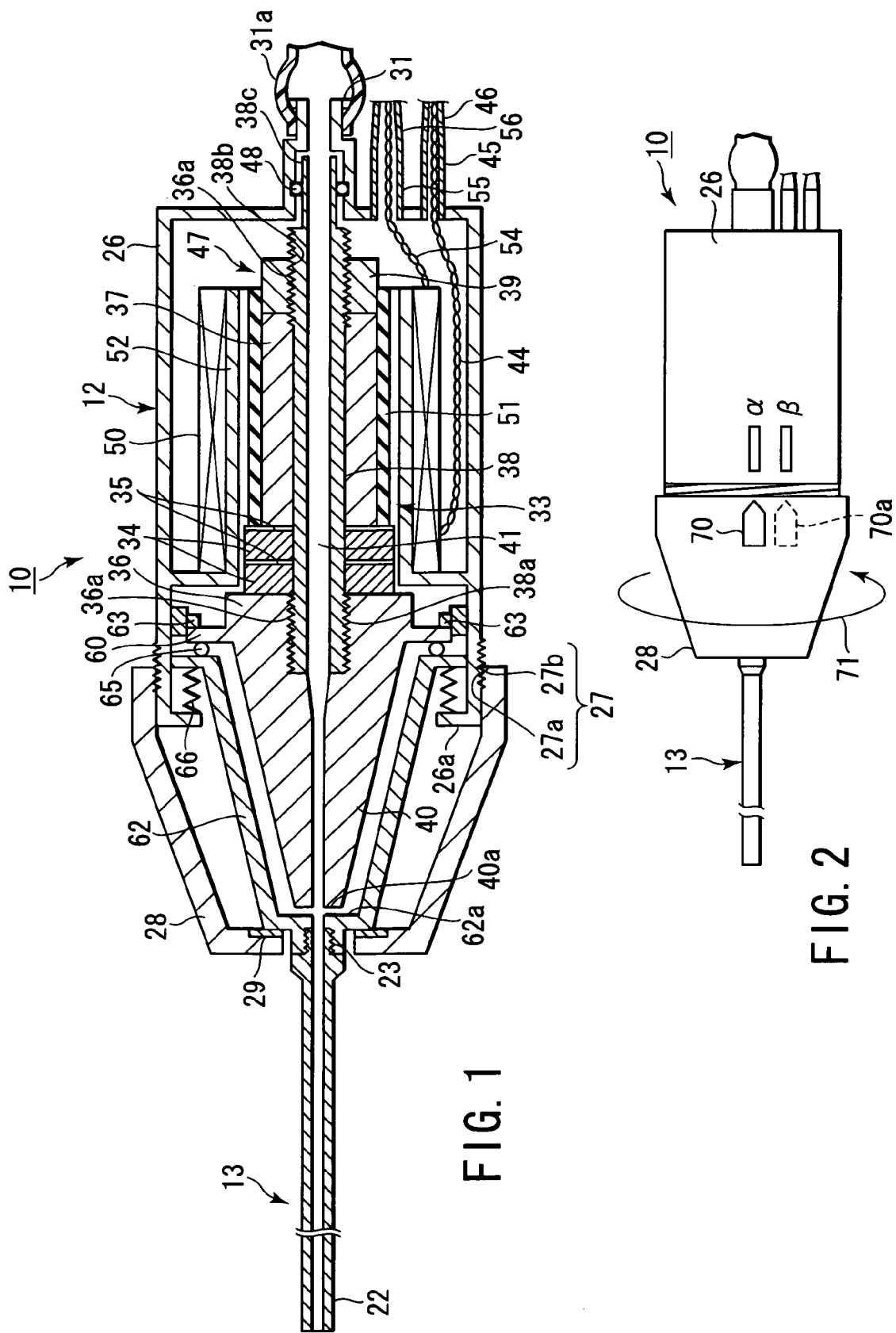

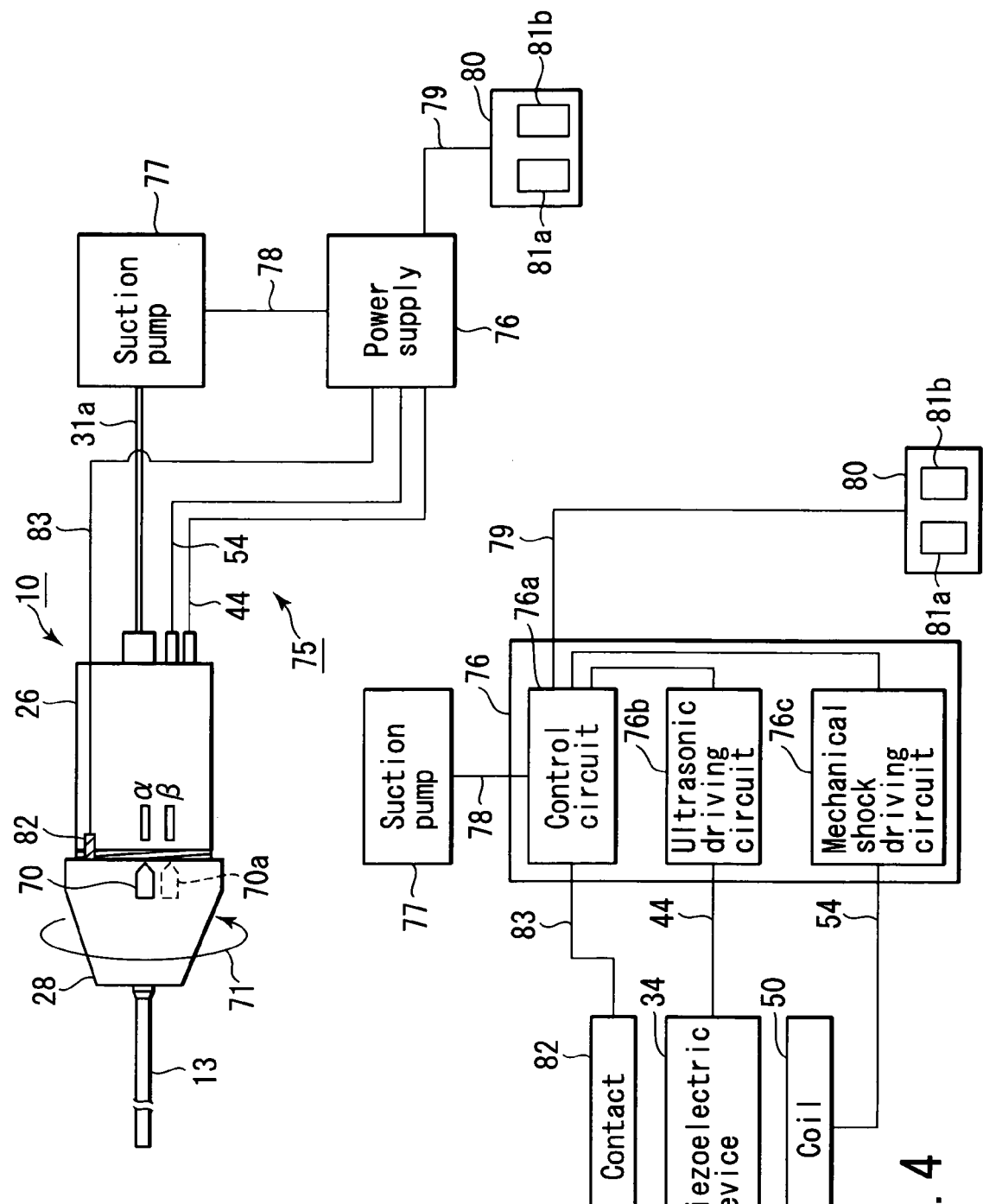

ENDOSCOPIC LITHOTRIPSY APPARATUS AND LITHOTRIPSY METHOD OF TREATMENT OBJECT USING THE APPARATUS

CROSS-REFERENCE TO RELATED APPLICATIONS

This application is based upon and claims the benefit of priority from the prior Japanese Patent Application No. 2002-352702, filed Dec. 4, 2002, the entire contents of which are incorporated herein by reference.

BACKGROUND OF THE INVENTION

1. Field of the Invention

The present invention relates to an endoscopic lithotripsy apparatus and a lithotripsy method of a treatment object using the endoscopic lithotripsy apparatus, in which a probe is inserted in to a body cavity to crush/treat solid matter such as a urinary calculus.

2. Description of the Related Art

For example, as disclosed in Jpn. Pat. Appln. KOKAI Publication No. 61-268244, an ultrasonic lithotripsy apparatus has heretofore been known which applies an ultrasonic vibration to a calculus produced in a body cavity under an endoscope to crush the calculus. Additionally, for example, as disclosed in U.S. Pat. Nos. 5,722,980 and 6,149,656, a mechanical shock type lithotripsy apparatus has also been known, which applies a mechanical shock to a probe under the endoscope to crush the calculus.

BRIEF SUMMARY OF THE INVENTION

According to one aspect of the present invention, there is provided an endoscopic lithotripsy probe apparatus including a probe, ultrasonic vibration source, mechanical shock generation source, and switch mechanism. The ultrasonic vibration source is detachably attached to the probe to transmit an ultrasonic vibration to the probe in a state in which the proximal end of the probe is connected to the ultrasonic vibration source. The mechanical shock generation source, which is disposed on the side of the proximal end of the probe, applies a force to the ultrasonic vibration source in a state in which the ultrasonic vibration source is detached from the proximal end of the probe, and allows the ultrasonic vibration source to collide with the proximal end of the probe so that a mechanical shock is applied to the probe. The switch mechanism switches a state in which the ultrasonic vibration from the ultrasonic vibration source is transmitted to the probe and a state in which the mechanical shock from the mechanical shock generation source is transmitted.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic sectional view of a lithotripsy probe apparatus according to a first embodiment;

FIG. 2 is a schematic appearance view showing the lithotripsy probe apparatus according to the first embodiment;

FIG. 3 is a schematic diagram showing the lithotripsy probe apparatus in a lithotripsy system of the lithotripsy probe apparatus according to a second embodiment, and a connected state of a power supply and suction pump connected to the lithotripsy probe apparatus;

FIG. 4 is a block diagram showing an electric connection state of the lithotripsy probe apparatus, power supply, and suction pump in the lithotripsy system according to the second embodiment;

DETAILED DESCRIPTION OF THE INVENTION

Figure 5:
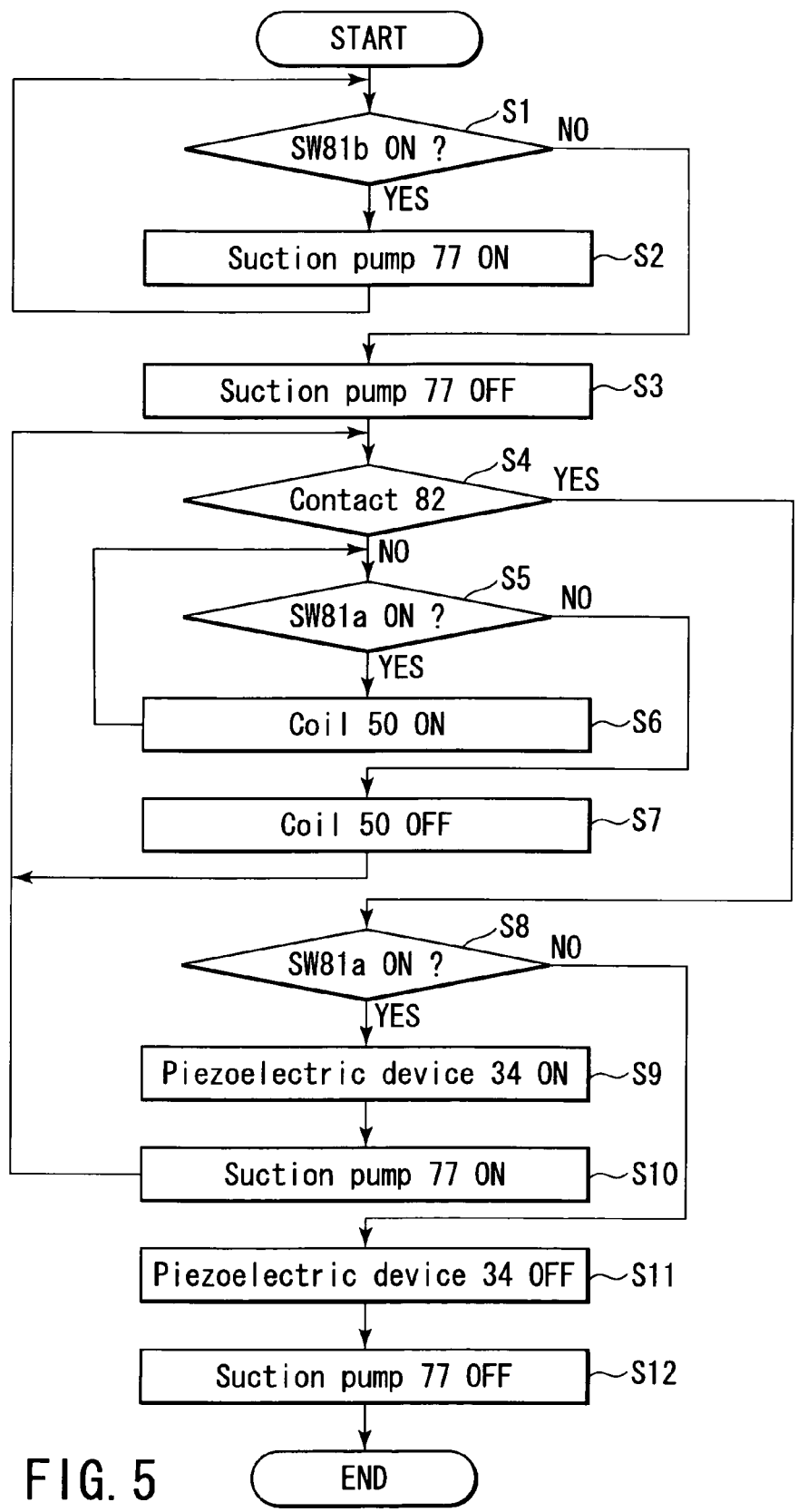
FIG. 5 is a schematic flowchart showing a function in using the lithotripsy system according to the second embodiment.

Preferable embodiments of the present invention will hereinafter be described with reference to the drawings.

First, a first embodiment will be described with reference to FIGS. 1 and 2.

As shown in FIG. 1, a lithotripsy probe apparatus 10 disposed in an endoscopic lithotripsy apparatus according to the present embodiment includes: a grasp section 12 grasped by an operator; and an elongated probe (insertion section) 13 to be inserted into a body cavity via an endoscope (not shown).

The probe 13 includes a pipe 22 which includes a screw portion 23 in a proximal end and which is formed of a metal material. This pipe 22 is detachably attached to a coupling member 62 described later, disposed in a distal end of the grasp section 12, via the screw portion 23. Therefore, the proximal end of the probe 13 is connected to the distal end of the grasp section 12.

The grasp section 12 includes an outer case 26, for example, having a cylindrical shape, which is to be grasped by the operator. A male screw portion 27a is formed on an outer peripheral surface of the distal end of the outer case 26. A cover member 28 whose distal end is opened is disposed on the front side of the outer case 26. The cover member 28 has a substantially conical or truncated conical shape, and is formed to be hollow. A female screw portion 27b attachable to the male screw portion 27a of the outer case 26 is disposed in the inner peripheral surface of the proximal end of the cover member 28. Therefore, the male screw portion 27a of the outer case 26 is fitted in the female screw portion 27b of the cover member 28 to form a screw portion 27, and mutual relative positions of the outer case 26 and cover member 28 are fixed. That is, when the cover member 28 is rotated with respect to the outer case 26, the cover member 28 moves along a central axis of the outer case 26. An elastic member 29, for example, having an annular shape is disposed on an inner surface of the cover member 28 in the vicinity of an opening in the cover member 28. The distal end of the coupling member 62 described later abuts on the elastic member 29.

A flange portion 26a projecting toward a central axis direction of the outer case 26 is disposed on the distal end of the outer case 26. One end of a spring 66 is disposed on the flange portion 26a. A pipe-shaped cap 31 projecting rearwards is disposed on the central axis of a rear end (rear end wall) of the outer case 26. The cap 31 is connected to one end of a suction tube 31a whose other end is connected to a suction pump (not shown) which is a suction source.

An ultrasonic vibration source which transmits an ultrasonic vibration to the probe 13, and a mechanical shock generation source which transmits a mechanical shock to the probe are switchably disposed inside the outer case 26.

A Langevin type ultrasonic vibrator 33 is disposed as an ultrasonic vibration source in a central part of the inside of the outer case 26. Inside the outer case 26, a coil 50 is disposed as a mechanical shock generation source which applies a force along the central axis of the outer case 26 to move the ultrasonic vibrator 33 in an outer peripheral position of the ultrasonic vibrator 33.

The ultrasonic vibrator 33 includes, for example, a pair of piezoelectric devices 34, a pair of electrode plates 35, a pair of metal blocks 36, 37, a bolt portion 38, and a nut 39. The pair of piezoelectric devices 34 and the pair of electrode plates 35 are formed in the same circular ring shape. These piezoelectric devices 34 are juxtaposed on the central axis of the circular ring (the central axis of the pipe 22). One electrode plate 35 is disposed between the juxtaposed piezoelectric devices 34. That is, one electrode plate 35 is held by one pair of the piezoelectric devices 34. The other electrode plate 35 abuts on the rear-side piezoelectric device 34 on a side apart from the probe 13 (rear side). The other electrode plate 35 is held by the rear-side piezoelectric device 34 and the cylindrical rear-side metal block 37. Therefore, the distal end of the rear-side metal block 37 abuts on the other electrode plate 35.

The proximal end of the cylindrical front-side metal block 36 abuts on the piezoelectric device 34 on the side apart from the rear-side metal block 37 (front side). In this front-side metal block 36, a substantially truncated conical horn 40 is formed integrally with the front-side metal block 36. A hole is formed along the central axis of an inner hole of the pipe 22 of the probe 13 in these piezoelectric devices 34, electrode plates 35, front and rear metal blocks 36, 37, and horn 40. The hole inside the piezoelectric devices 34, electrode plates 35, and front and rear metal blocks 36, 37 is formed to be larger than the inner hole of the pipe 22.

A female screw portion 36a is formed in the inner peripheral surface of the hole on the central axis of the front-side metal block 36. This female screw portion 36a engages with the distal end of the bolt portion 38 including male screw portions 38a, 38b on the distal end and proximal end, respectively. A through hole 41 communicating with the inner hole of the pipe 22 is formed inside the bolt portion 38. The through hole 41 is formed to have a diameter larger than that of the inner hole of the pipe 22.

The bolt portion 38 extends through the front-side metal block 36, piezoelectric devices 34, electrode plates 35, and rear-side metal block 37. The nut 39 is attached to the male screw portion 38b of the proximal end of the bolt portion 38. Therefore, the nut 39 abuts on the rear end of the rear-side metal block 37. When the nut 39 is firmly attached to the male screw portion 38b of the proximal end of the bolt portion 38, the rear-side metal block 37 is pressed on the side of the horn 40. Therefore, since the nut 39 is screwed to the bolt portion 38, the rear-side metal block 37, electrode plates 35, piezoelectric devices 34, and front-side metal block 36 are fixed in a mutually pressed state, while a force is applied toward the distal end of the horn 40. As a result, the ultrasonic vibration produced from the piezoelectric device 34 is efficiently transmitted to the horn 40. The horn 40 enlarges the ultrasonic vibration generated from the piezoelectric devices 34 toward the distal end from the proximal end.

The electrode plates 35 are connected, for example, to a two-core lead wire 44. The lead wire 44 is passed through the rear end wall of the outer case 26 and is guided into an external power supply (not shown). A duct for lead 45 through which the lead wire 44 is passed is disposed on the rear end wall of the outer case 26 through which the lead wire 44 is passed. An elastic tube for break prevention 46 which prevents disconnection of the lead wire 44 is attached to the rear end of the duct for lead 45.

In this manner, an ultrasonic vibrator unit 47 is formed as an integrated component of the ultrasonic vibrator 33.

A thin-wall cylindrical portion 38c having an outer diameter smaller than that of a middle part of the bolt portion 38 is integrally disposed on the proximal end of the bolt portion 38. An inner hole diameter of the thin-wall cylindrical portion 38c is the same as that of the bolt portion 38 and these portions are on the same plane. An O ring 48 is disposed between the outer peripheral surface of the thin-wall cylindrical portion 38c and the inner peripheral surface of the cap 31. Therefore, watertightness is provided so as to prevent sucked solid matters crushed in the distal end of the pipe 22 and solution from entering a portion other than the through hole 41.

A cylindrical metal frame 51 is bonded to the outer periphery of the rear-side metal block 37 and nut 39 of the ultrasonic vibrator 33 so as to be easily influenced by a magnetic field produced by passing a current through the coil 50 which is the mechanical shock generation source.

A support portion 52 projecting integrally from the outer case 26 on an inward side is disposed in an outer peripheral position apart from the metal frame 51 in the outer peripheral surface of the ultrasonic vibrator 33 inside the outer case 26. The coil 50 is disposed on the outer periphery of the support portion 52 to change the magnetic field as the mechanical shock generation source, when the current is passed. This coil 50 is connected, for example, to a two-core lead wire 54. The lead wire 54 is passed through the rear end wall of the outer case 26 and guided into the external power supply (not shown). A duct for lead 55 through which the lead wire 54 is passed is disposed on the rear end wall of the outer case 26 through which the lead wire 54 is passed. An elastic tube for break prevention 56 which prevents the disconnection of the lead wire 54 is attached to the rear end of the duct for lead 55.

A flange portion 60 projecting outwards in a diametric direction toward the front-side metal block 36 is formed integrally on the outer peripheral surface of the horn 40 of the distal end of the ultrasonic vibrator 33 and on the outer peripheral surface of the distal end of the front-side metal block 36. The coupling member 62 formed in such a shape as to cover the horn 40 is bonded to the flange portion 60. Concretely, a portion positioned in a node of vibration in a case where the vibration of the ultrasonic vibrator 33 is transmitted to the horn 40, the rear side of the flange portion 60 herein, is positioned by screws 63, and in this state the flange portion 60 is supported with respect to the outer case 26. An O ring 65 is disposed between the front side of the flange portion 60 and the coupling member 62 to prevent the solid matters crushed in the distal end of the pipe 22 or the solution from entering the portion other than the through hole 41. The O ring 65 is formed of elastically deformable polymeric resin materials such as a silicone rubber material. Therefore, the horn 40 is movable between the screws 63 and the coupling member 62 by the elastic deformation of the O ring 65.

For example, the spring 66 is disposed as an elastic material between the vicinity of the proximal end of the coupling member 62 and the flange portion 26a disposed on the distal end of the outer case 26 so as to urge the coupling member 62 on the rear side of the outer case 26. One end of the spring 66 is supported by the flange portion 26a of the outer case 26 as described above. The other end of the spring 66 is supported by the proximal end of the coupling member 62. Therefore, the shock transmitted both to the coupling member 62 and the outer case 26 is absorbed by the spring 66, O ring 65, and elastic member 29 described later.

The distal end of the coupling member 62 is allowed to abut on the elastic member 29 of the cover member 28 on whose inner surface the elastic member 29 is disposed. The proximal end of the pipe 22 is disconnectably connected to the distal end of the coupling member 62 by the screw portion 23. Therefore, the through hole 41 of the ultrasonic vibrator unit 47 and horn 40, the inner hole of the pipe 22, and the inner hole of the cap 31 are coaxially disposed to communicate with one another. This forms a suction hole via which the distal end of the pipe 22 communicates with the inner hole of the cap 31.

FIG. 2 shows the appearance of the lithotripsy probe apparatus 10. A mark 70 is disposed on the outer surface of the cover member 28. Marks α, β are displayed on the outer surface of the outer case 26. As shown in FIG. 2, when the cover member 28 is rotated in a direction of an arrow 71 in FIG. 2 from an aligned state of the mark 70 with the mark α, the mark 70 is rotated to a position of a mark 70a shown by a broken line in FIG. 2 to align the mark 70 with the position of the mark β.

FIG. 1 shows that the mark 70 in FIG. 2 is aligned with the mark α. At this time, as shown in FIG. 1, an inner surface 62a of the coupling member 62 is disposed apart from a distal end surface 40a of the horn 40. When the cover member 28 is rotated so as to align the mark 70 with the mark β, the inner surface 62a of the coupling member 62 is closely attached to the distal end surface 40a of the horn 40 in FIG. 1, and the ultrasonic vibration can be transmitted to the pipe 22 of the probe 13.

Therefore, the cover member 28 includes a function of a switch mechanism to switch a closely attached state (abutting state) in which the proximal end of the pipe 22 adheres to the distal end surface 40a of the horn 40 in contact with the ultrasonic vibration source (ultrasonic vibrator 33) and a detached state in which the proximal end of the pipe 22 is detached from the distal end surface 40a of the horn 40 of the Langevin type ultrasonic vibrator 33 driven by the mechanical shock generation source by relative rotation with respect to the outer case 26.

The cover member 28 further functions as an adjustment mechanism by which a connected/disconnected state of the distal end surface 40a of the horn 40 functioning by the pipe 22 and the ultrasonic vibration source or the mechanical shock generation source is adjustable with respect to the inner surface 62a of the coupling member 62. Therefore, the ultrasonic vibration is transmitted to the pipe 22 in the closely attached state, and the mechanical shock force is transmitted to the pipe 22 because of rapid shift to the abutment state in the detached state. Therefore, the ultrasonic vibration and the mechanical shock force transmitted to the pipe 22 of the probe 13 are selectable.

Next, a method of using the lithotripsy probe apparatus 10 will be described as the function of the lithotripsy probe apparatus 10 according to the present embodiment with reference to FIGS. 1 and 2.

First, the probe 13 of the lithotripsy probe apparatus 10 is guided into the body cavity via an endoscope. In this state, the cover member 28 is rotated with respect to the outer case 26, and the mark 70 is aligned with the mark α. The proximal end of the pipe 22 and the distal end surface 40a of the horn 40 of the ultrasonic vibrator 33 driven by the mechanical shock generation source are brought into the detached state (see FIG. 1).

In this state, an appropriate pulse-like power is supplied to the coil 50 from the power supply (not shown) via the lead wire 54. A magnetic field of the portion where the ultrasonic vibrator unit 47 is disposed inside the coil 50 changes. The metal frame 51 is influenced by the magnetic field generated by the coil 50. Therefore, the ultrasonic vibrator unit 47 disposed on the inner periphery of the metal frame 51 undergoes the force toward the front (distal end of the probe 13) to rapidly move, and the distal end surface 40a of the horn 40 collides with the inner surface 62a of the coupling member 62. The mechanical shock force is transmitted toward the distal end from the proximal end of the pipe 22 of the probe 13. This mechanical shock force is transmitted to a calculus from the distal end of the pipe 22, and a hard or large calculus is broken. At this time, the shock of the collision of the horn 40 with the coupling member 62 is absorbed by the O ring 65, spring 66, and elastic member 29. Therefore, the shock force transmitted to operator's hands is transmitted in a largely decreased state as compared with energy at the time of the collision.

Next, the cover member 28 is rotated with respect to the outer case 26 to align the mark 70 with the mark β. The cover member 28 moves backwards with respect to the outer case 26 to urge the coupling member 62 rearwards by the spring 66. At this time, since the elastic member 29 contacts the surface of the coupling member 62 opposite to the inner surface 62a, the cover member moves in such a direction as to compress the O ring 65, and the inner surface 62a of the coupling member 62 is allowed to abut on the distal end surface 40a of the horn 40. Therefore, the proximal end of the pipe 22 and the distal end surface 40a of the horn 40 contacting the ultrasonic vibration source (ultrasonic vibrator 33) are brought into the closely attached state.

A high-frequency current is outputted from the power supply (not shown) in this state to make a potential difference between one pair of electrode plates 35 via the lead wire 44, and the piezoelectric device 34 is driven (ultrasonically vibrated). The ultrasonic vibration generated by the vibration of the piezoelectric devices 34 is transmitted to the front-side metal block 36, and amplitude is increased by the horn 40. Since the distal end surface 40a of the horn 40 adheres to the inner surface 62a of the coupling member 62, the high-frequency ultrasonic vibration is transmitted to the proximal end of the pipe 22 of the probe 13 disposed in the distal end of the coupling member 62. The ultrasonic vibration is transmitted to the calculus from the distal end of the pipe 22, the hard calculus or the calculus broken by the mechanical shock force is further crushed, and the calculus is finely divided.

In this closely attached state, the calculus is further finely crushed by the ultrasonic vibration, and moreover a suction pump (not shown) is also operated. Therefore, the crushed calculus is sucked/removed via the inner hole of the pipe 22 and the through hole 41.

The crushing by the mechanical shock force transmitted to the pipe 22 of the probe 13 is sometimes omitted depending on a size of calculus. For example, when the calculus is small, the force may be transmitted to the pipe 22 to crush the calculus by the ultrasonic vibration.

As described above, the following effect is obtained by the lithotripsy probe apparatus 10 according to the present embodiment.

When the cover member 28 is rotated to switch the mark 70 disposed on the cover member 28 to the positions of the marks α, β disposed on the outer case 26, the force applied to the probe 13 can surely be switched to the mechanical shock force and the ultrasonic vibration. Therefore, the force of each desired system can be transmitted to the pipe 22.

When the solid matters such as the large calculus are assumed as crushing objects, first the cover member 28 is rotated and positioned with respect to the outer case 26 to perform treatment in such a manner that the mechanical shock force is transmitted to the calculus to crush the calculus. Next, the position is similarly set to perform the treatment in such a manner that the ultrasonic vibration is transmitted to the crushed calculus to further finely crush the calculus. Then, the finely divided calculus can be sucked/removed via the through hole 41. In this manner, both the mechanical shock type and the ultrasonic vibration type can selectively be used with one lithotripsy probe apparatus 10, the probe 13 of the lithotripsy probe apparatus 10 does not have to be replaced with respect to the endoscope, and therefore a time for the crushing can be reduced.

Next, a second embodiment of the present invention will be described with reference to FIGS. 3 to 5. Since this embodiment is a modification example of the first embodiment, the same members as those described in the first embodiment are denoted with the same reference numerals, and detailed description is omitted.

As shown in FIG. 3, an endoscopic lithotripsy apparatus 75 includes the lithotripsy probe apparatus 10, a power supply 76, and a suction pump 77. The power supply 76 is connected to the suction pump 77 via a signal line 78. The power supply 76 is connected to a foot switch 80 via a cable 79. The foot switch 80 includes an output switch 81a and pump switch 81b.

Contacts 82 are disposed on a part of the outer peripheral surface in the vicinity of the distal end of the outer case 26 of the lithotripsy probe apparatus 10 and a part of the inner peripheral surface in the vicinity of the rear end of the cover member 28. The contacts 82 contact each other (ON state) in a position where the mark 70 of the cover member 28 is aligned with the mark β of the outer case 26. The contact 82 disposed on the outer case 26 is electrically connected to the power supply 76 by a lead wire 83.

As shown in FIG. 4, the power supply 76 includes a control circuit 76a, ultrasonic driving circuit 76b, and mechanical shock driving circuit 76c. The control circuit 76a is connected to the ultrasonic driving circuit 76b, mechanical shock driving circuit 76c, suction pump 77, and foot switch 80. These circuits 76b, 76c, suction pump 77, and foot switch 80 are controlled by the control circuit 76a. Therefore, the output switch 81a of the foot switch 80 is an input device which inputs a signal to the control circuit 76a to supply a power for generating the ultrasonic vibration or the mechanical shock force to the piezoelectric devices 34 or the coil 50. The pump switch 81b is an input device which inputs a signal into the control circuit 76a to supply the power for operating the suction pump 77. It is to be noted that the suction pump 77 is driven/controlled, when the ultrasonic driving circuit 76b is driven/controlled by the control circuit 76a.

The control circuit 76a is connected to the contact 82 of the outer case 26 by the lead wire 83. Therefore, the contacts 82 of the outer case 26 and cover member 28 are input devices which inputs a signal into the control circuit 76a to determine whether to supply the power outputted for generating the ultrasonic vibration or the mechanical shock force to the piezoelectric devices 34 or the coil 50.

Then, when the power supply 76 is used to generate the ultrasonic vibration, for the power for the ultrasonic vibration, the output from the ultrasonic driving circuit 76b of the power supply 76 is transmitted to the piezoelectric device 34 via the lead wire 44. When the power supply 76 is used to generate the mechanical shock force, for the power which generates the mechanical shock force, the output from the mechanical shock driving circuit 76c of the power supply 76 is transmitted to the coil 50 via the lead wire 54.

The function of the endoscopic lithotripsy apparatus 75 according to the present embodiment constituted as described above will be described with reference to FIGS. 3 to 5.

The mark 70 of the cover member 28 is aligned with the mark α of the outer case 26. The proximal end of the pipe 22 is brought into the detached state from the distal end surface 40a of the horn 40 of the Langevin type ultrasonic vibrator 33 driven by the mechanical shock generation source. In this state, since the contacts 82 of the outer case 26 and cover member 28 do not contact each other, the signal has an OFF state. Therefore, the control circuit 76a of the power supply 76 has such a state as to be capable of outputting only the power for generating the mechanical shock force. Here, when the output switch 81a of the foot switch 80 is operated, the signal is inputted into the control circuit 76a. Then, the signal is transmitted to the mechanical shock driving circuit 76c from the control circuit 76a, and the power is supplied to the coil 50 via the lead wire 54. Therefore, the ultrasonic vibrator unit 47 moves to allow the distal end surface 40a of the horn 40 to collide with the inner surface 62a of the coupling member 62, and the mechanical shock force is transmitted to the pipe 22. Since the signal of the contact 82 has the OFF state, the suction pump 77 does not operate. It is to be noted that when the pump switch 81b of the foot switch 80 is operated, the suction pump 77 operates regardless of the positions of the marks 70, α, β.

Next, the mark 70 of the cover member 28 is aligned with the mark β of the outer case 26. The closely attached state is obtained in which the proximal end of the pipe 22 adheres to the distal end surface 40a of the horn 40 in contact with the ultrasonic vibration source. In this state, since the contacts 82 of the outer case 26 and cover member 28 contact each other, the signals of the contacts 82 have the ON state. Therefore, the control circuit 76a of the power supply 76 is brought in such a state that the ultrasonic vibration is generated and the power for operating the suction pump 77 can be outputted. Here, when the output switch 81a of the foot switch 80 is operated here, the signal is inputted into the control circuit 76a. The signal is transmitted to the ultrasonic driving circuit 76b from the control circuit 76a to supply the power to the piezoelectric device 34 via the lead wire 44. Therefore, the ultrasonic vibration is transmitted to the pipe 22. Moreover, the suction pump 77 operates together with the ultrasonic driving circuit 76b to such the crushed calculus.

An operation state of the control circuit 76a will be described with reference to a flowchart shown in FIG. 5.

First it is judged whether or not the pump switch 81b of the foot switch 80 is ON (S1). When the pump switch 81b is ON, the suction pump 77 is operated (S2). It is again judged whether or not the pump switch 81b is ON. On the other hand, when the pump switch 81b is OFF, the suction pump 77 is not operated (S3).

When the suction pump 77 is not operated, it is judged whether or not the contacts 82 of the outer case 26 and cover member 28 are ON (S4). When the contacts 82 are OFF, it is judged whether or not the output switch 81a of the foot switch 80 is ON (S5). When the output switch 81a is ON, the mechanical shock driving circuit 76c is operated to supply the power to the coil 50 (S6). Therefore, the ultrasonic vibrator unit 47 moves to transmit the mechanical shock force to the pipe 22. It is again judged whether or not the output switch 81*a* is ON. On the other hand, when the output switch 81*a* is OFF, the mechanical shock driving circuit 76*c* is not operated (S7). It is again judged whether or not the contacts 82 are ON (S4).

When the contacts 82 are ON, it is judged whether or not the output switch 81*a* of the foot switch 80 is ON (S8). When the output switch 81*a* is ON, the ultrasonic driving circuit 76*b* is operated to supply the power to the piezoelectric devices 34 (S9). The power is supplied to the suction pump 77 to suck the crushed calculus or the solution (S10). It is again judged whether or not the contacts 82 are ON (S4).

When the contacts 82 are ON and the output switch 81*a* of the foot switch 80 is OFF, the ultrasonic driving circuit 76*b* is not operated (S11). The suction pump 77 is not also operated (S12).

As described above, the following effect is obtained by the endoscopic lithotripsy apparatus 75 according to the embodiment. The description of the same effect as that described with respect to the lithotripsy probe apparatus 10 of the first embodiment will be omitted.

The ON/OFF of the contacts 82 is defined by the positions of the marks $\alpha$, $\beta$ of the outer case 26 with respect to the mark 70 of the cover member 28. Therefore, the contacts 82 can be allowed to function as a position detection mechanism which detects the positions of the marks $\alpha$, $\beta$ with respect to the mark 70, that is, which detects the position of the cover member 28 capable of generating the ultrasonic vibration and the mechanical shock force. The contacts can also function as a detection mechanism which detects the detached state and closely attached state of the distal end surface 40*a* of the horn 40 with respect to the inner surface 62*a* of the coupling member 62. Since the contacts 82 can be switched to ON/OFF, the ON/OFF of the suction pump 77 can accordingly automatically be switched.

Therefore, when the distal end surface 40*a* of the horn 40 and the inner surface 62*a* of the coupling member 62 are in the detached state, the suction pump 77 does not operate except that the pump is forcibly operated so as to operate the pump switch 81*b*. Therefore, clogging by the large calculus, and the like stuck into the through hole 41 can be prevented.

Next, a third embodiment of the present invention will be described with reference to FIG. 6.

Figure 6:
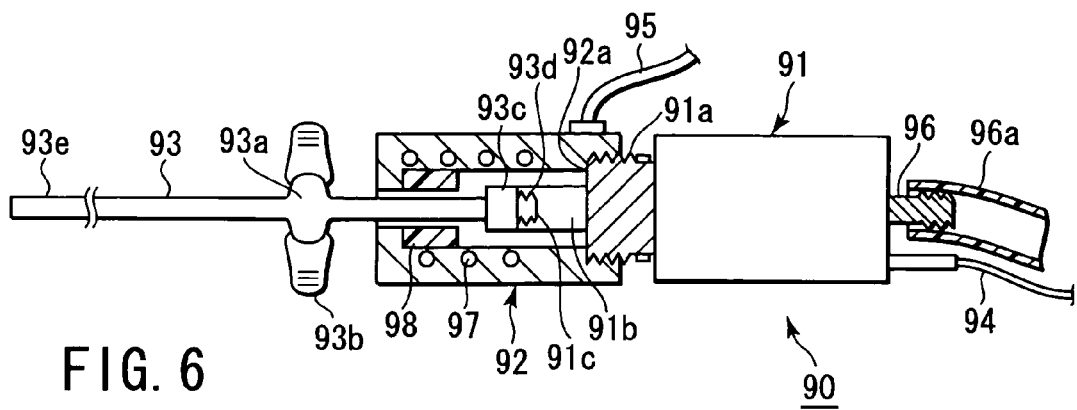
FIG. 6 is a schematic partial sectional view of a hand piece in an endoscopic lithotripsy apparatus according to a third embodiment.

FIG. 6 shows a schematic sectional view of a hand piece (lithotripsy probe apparatus) 90 in the endoscopic lithotripsy apparatus of the third embodiment. FIG. 6 is a sectional view of only a central part of the description of the constitution.

The hand piece 90 includes an ultrasonic vibration source 91, mechanical shock generation source 92, and crushing probe (insertion portion) 93, for example, of a metal material. The crushing probe 93 has a pipe shape. A handle attaching portion 93*a* to which a handle 93*b* is attached is disposed on the outer peripheral surface of the crushing probe 93.

The ultrasonic vibration source 91 is covered with a cover. A hole (not shown) is disposed along the central axis of the ultrasonic vibration source 91. The mechanical shock generation source 92 includes a ultrasonic vibration source fixing mechanism which is capable of fixing the ultrasonic vibration source 91. Therefore, the ultrasonic vibration source 91 can be fixed to the mechanical shock generation source 92. Here, a male screw portion 91*a* is disposed as the ultrasonic vibration source fixing mechanism on the distal end of the cover of the ultrasonic vibration source 91. A female screw portion 92*a* is disposed on the proximal end of the mechanical shock generation source 92. Therefore, since the screw portions 91*a*, 92*a* are screwed onto each other, the ultrasonic vibration source 91 is fixed to the mechanical shock generation source 92.

An ultrasonic vibration source cap 91*b* is disposed on the distal end of the ultrasonic vibration source 91. A female screw portion 91*c* is disposed on the inner peripheral surface of the cap 91*b*. A crushing probe cap 93*c* is disposed on the proximal end of the crushing probe 93. A male screw portion 93*d* is disposed on the outer peripheral surface of the cap 93*c*. Therefore, the ultrasonic vibration source 91 can mutually be screwed onto the crushing probe 93 by the screw portions 91*c*, 93*d*. To attach/detach these screw portions 91*c*, 93*d*, the handle 93*b* attached to the handle attaching portion 93*a* disposed on the crushing probe 93 is used. When the handle 93*b* is rotated/operated around the axis of the crushing probe 93, the closely attached state and the detached state between the crushing probe 93 and the ultrasonic vibration source 91 are switched to adjust the attached/detached state. Therefore, the handle 93*b* and the caps 91*b*, 93*c* function as the adjustment mechanism which adjusts the attached/detached state between the proximal end of the crushing probe 93 and the male screw portion 91*a* of the ultrasonic vibration source 91. Therefore, the ultrasonic vibration is transmitted in the closely attached state. The mechanical shock force is transmitted in the detached state. Then, the screw portions 91*c*, 93*d* function as the switch mechanism of the ultrasonic vibration source and mechanical shock generation source.

A driving cable for ultrasonic crushing 94 connected to the ultrasonic vibration source 91 is connected to the ultrasonic driving circuit 76*b* (see FIG. 4). A driving cable for mechanical shock crushing 95 connected to the mechanical shock generation source 92 is connected to the mechanical shock driving circuit 76*c* (see FIG. 4). A cap 96 disposed on the rear end of the ultrasonic vibration source 91 is connected to the suction pump 77 (see FIG. 4) via a suction tube 96*a*.

A conductive coil 97 is disposed in the mechanical shock generation source 92. Therefore, when the output from the ultrasonic driving circuit 76*b* and that from the mechanical shock driving circuit 76*c* are switched, the ultrasonic vibration and mechanical shock force are transmitted toward a distal end 93*e* from the proximal end of the probe 93.

An elastic member 98 is disposed on the distal end of an inner peripheral portion of the coil 97 to fulfill a function of limiting an operation range of the crushing probe 93 and returning the crushing probe 93 to an original position after generation of the shock force.

The function of the hand piece 90 of the endoscopic lithotripsy apparatus according to the present embodiment will be described in the constitution described above.

To perform the mechanical shock crushing in the distal end 93*e* of the probe 93, the handle 93*b* is grasped to detach the crushing probe 93 from the cap 91*b* of the ultrasonic vibration source 91. Then, the probe 93 is slidable in a length direction (axial direction) inside the mechanical shock generation source 92. A driving power for generating the mechanical shock is supplied to the mechanical shock generation source 92 via the driving cable for mechanical shock crushing 95. When a current flows through the coil 97 of the mechanical shock generation source 92, a changing electromagnetic force is used to move the crushing probe 93. The shock by this movement is transmitted to the calculus from the distal end 93*e* of the crushing probe 93 to break the calculus. When the mechanical shock force is generated, the crushing probe cap 93*c* abuts on (collides with) the elastic member 98, and the crushing probe 93 is returned to the original position by an elastic reaction force at this time. When the current is passed through the coil 97 in a direction opposite to the above-described direction, the crushing probe 93 is pulled rearwards and returned to the original position.

To perform the ultrasonic crushing, the handle 93b is held and caps 91b, 93c are used to firmly fix the crushing probe 93 and ultrasonic vibration source 91. A high-frequency current is supplied to the ultrasonic vibration source 91 via the driving cable for ultrasonic crushing 94 to generate the ultrasonic vibration. The ultrasonic vibration generated by the ultrasonic vibration source 91 is transmitted to the crushing probe 93 via both the caps 91b, 93c. Finally, the distal end 93e of the crushing probe 93 is ultrasonically driven, and the vibration is used to crush the calculus in contact with the distal end 93e of the crushing probe 93. The crushed calculus is sucked from an inner cavity of the distal end 93e of the crushing probe 93 using a suction force of the suction pump 77, and recovered through the cap 96 and suction tube 96a via the inner cavities of the crushing probe 93 and ultrasonic vibration source 91.

As described above, the hand piece 90 of the endoscopic lithotripsy apparatus according to the present embodiment obtains the following effect.

When the handle 93b is rotated/operated around the axis of the crushing probe 93, the crushing probe 93 may be fixed to the ultrasonic vibration source 91, or the crushing probe 93 may be detached from the ultrasonic vibration source 91 and may freely be moved in the length direction (axial direction). Therefore, the ultrasonic vibration and mechanical shock force can appropriately be switched to transmit the respective forces to a pipe which is the crushing probe 93.

Therefore, when the large calculus is assumed as the crushing object, first the mechanical shock force is transmitted to the calculus via the crushing probe 93 to crush the calculus. Next, the ultrasonic vibration is transmitted to the crushed calculus via the crushing probe 93 to further finely crush the calculus, while the suction force of the suction pump 77 is used to suck/remove the calculus. Therefore, when the solid matters are crushed into small pieces, the crushing probe 93 does not have to be replaced, and therefore the time required for the crushing can be reduced.

Next, a fourth embodiment of the present invention will be described with reference to FIG. 7. Since this embodiment is a modification example of the third embodiment, the same members as those described in the third embodiment are denoted with the same reference numerals, and the detailed description will be omitted.

Figure 7:
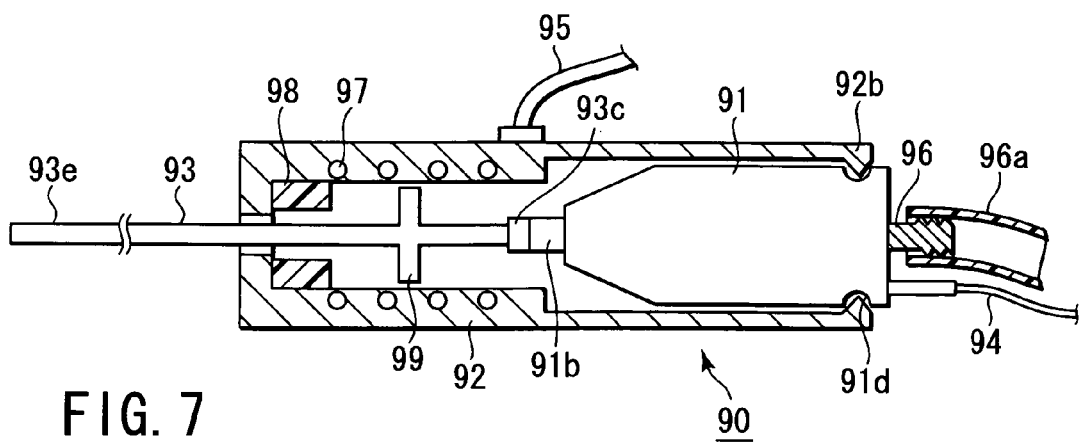
FIG. 7 is a schematic partial sectional view of the hand piece in the endoscopic lithotripsy apparatus according to a fourth embodiment

FIG. 7 shows a schematically partial sectional view of the hand piece (lithotripsy probe apparatus) 90 in the endoscopic lithotripsy apparatus of the fourth embodiment.

The hand piece 90 includes the ultrasonic vibration source 91, mechanical shock generation source 92, and crushing probe 93. The mechanical shock generation source 92 includes an ultrasonic vibration source temporary fixing mechanism to temporarily fix the ultrasonic vibration source 91. The crushing probe 93 includes a flange 99 projecting outwards in a diametric direction with respect to the axial direction of the crushing probe 93. The crushing probe 93 has a pipe shape.

A protrusion (convex portion) for temporary fixing 92b is disposed on the proximal end of the mechanical shock generation source 92. The protrusion 92b projects inwards in the diametric direction. A dent (concave portion) for the temporary fixing 91d is disposed on the proximal end of the ultrasonic vibration source 91. This dent 91d is disposed in a circumferential shape. Therefore, the ultrasonic vibration source 91 is temporarily fixed to the mechanical shock generation source 92, when the protrusion (convex portion) 92b disposed on the proximal end of the mechanical shock generation source 92 is mutually fitted in the dent (concave portion) 91d disposed in the proximal end of the ultrasonic vibration source 91. Therefore, the protrusion 92b and dent 91d function as the switch mechanism which switches the ultrasonic vibration and mechanical shock with respect to a treatment object.

The ultrasonic vibration source 91 can be screwed/fixed onto the crushing probe 93 by the ultrasonic vibration source cap 91b and crushing probe cap 93c. The screw portions 91c, 93d (see FIG. 6) are attached/detached using tools such as a wrench (not shown).

The driving cable for ultrasonic crushing 94 connected to the ultrasonic vibration source 91 is connected to the ultrasonic driving circuit 76b (see FIG. 4). The driving cable for mechanical shock crushing 95 connected to the mechanical shock generation source 92 is connected to the mechanical shock driving circuit 76c (see FIG. 4). The cap 96 disposed on the rear end of the ultrasonic vibration source 91 is connected to the suction pump 77 via the suction tube 96a.

The function of the hand piece 90 of the endoscopic lithotripsy apparatus according to the present embodiment constituted as described above will be described.

To perform the mechanical shock crushing, the ultrasonic vibration source 91 is further slightly pressed into the mechanical shock generation source 92 (forwards) with respect to the mechanical shock generation source 92 from a state in which the protrusion for the temporary fixing 92b is engaged with the dent for the temporary fixing 91d, and the protrusion 92b is disengaged from the dent 91d. The protrusion 92b is disposed on the rear end of the ultrasonic vibration source 91 including the dent 91d. Thereafter, the driving current for generating the mechanical shock is supplied to the coil 97 of the mechanical shock generation source 92 via the driving cable for mechanical shock crushing 95. When the current flows through the coil 97, the crushing probe 93 integrated with the ultrasonic vibration source 91 moves forwards by the electromagnetic force generated by the change of the magnetic field in the coil 97. The shock by this movement is transmitted to the calculus from the distal end 93e of the crushing probe 93 to break the calculus. It is to be noted that when the mechanical shock crushing is performed, the elastic member 98 abuts on the flange 99 of the crushing probe 93 to perform a function of limiting the operation range and returning the probe to the original position after the generation of the shock force.

Next, to perform the ultrasonic crushing as shown in FIG. 7, the protrusion for the temporary fixing 92b is engaged with the dent for the temporary fixing 91d to temporarily fix the ultrasonic vibration source 91 to the mechanical shock generation source 92. Thereafter, the high-frequency current is supplied to the ultrasonic vibration source 91 via the driving cable for the ultrasonic crushing 94 to generate the ultrasonic vibration. The ultrasonic vibration generated by the ultrasonic vibration source 91 is transmitted to the crushing probe 93 via both the caps 91b, 93c. Finally, the distal end 93e of the crushing probe 93 is ultrasonically vibrated, and the vibration is used to crush the calculus in contact with the distal end 93e of the crushing probe 93. At this time, the movement of the flange 99 disposed on the crushing probe 93 is not limited by the elastic member 98, and the flange can move in accordance with the movement of the crushing probe 93.

The crushed calculus is passed through the inner hole of the distal end 93e of the crushing probe 93 using the suction force of the suction pump 77, and recovered through the cap 96 and suction tube 96a via the inner hole of the crushing probe 93 and ultrasonic vibration source 91.

As described above, the hand piece 90 of the endoscopic lithotripsy apparatus according to the present embodiment obtains the following effect. It is to be noted that the same effect as that of the third embodiment will be omitted.

Without detaching the crushing probe 93 from the caps 91b, 93c, the engaged/non-engaged state between the protrusion for temporary fixing 92b and the dent for temporary fixing 91d is switched. Accordingly, the crushing system by the ultrasonic vibration and that by the mechanical shock force can be switched. Therefore, since the crushing probe 93 does not have to be replaced, the time required for the crushing treatment can be reduced.

Next, a fifth embodiment of the present invention will be described with reference to FIGS. 8 and 9.

Figure 8:
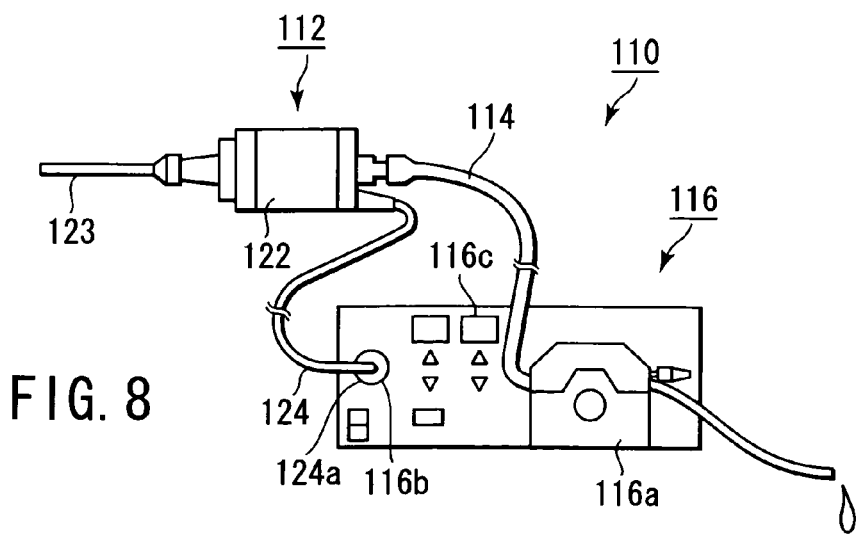
FIG. 8 is a schematic diagram showing a whole constitution of the lithotripsy system according to a fifth embodiment.

FIG. 8 shows a whole lithotripsy system 110. FIG. 9 shows a section of a lithotripsy probe apparatus 112.

As shown in FIG. 8, the lithotripsy system 110 includes the lithotripsy probe apparatus 112, a suction tube 114, and a power supply main body 116. The power supply main body 116 includes a suction pump 116a, a connector 116b, and an operation panel 116c. The end of the suction tube 114 is connected to the suction pump 116a.

As shown in FIG. 8, the lithotripsy probe apparatus 112 includes a grasp portion 122, probe (insertion portion) 123, and power supply cord 124. The power supply cord 124 extends from the rear end of the grasp portion 122, and includes a connection portion 124a connected to the connector 116b of the power supply main body 116. The probe 123 is disposed on the distal end of the grasp portion 122.

Figure 9:
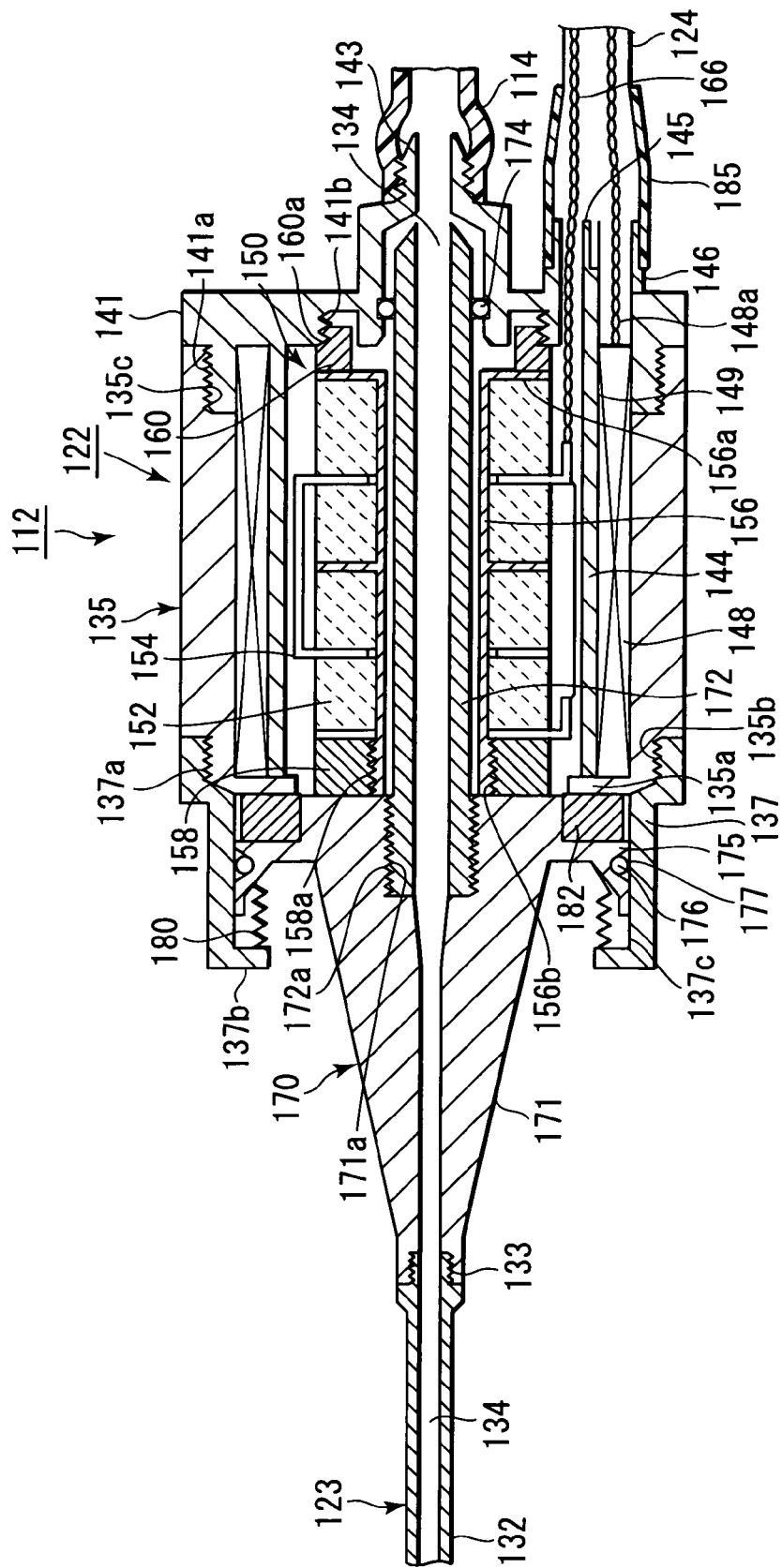
FIG. 9 is a schematic sectional view of the hand piece in the lithotripsy system according to the fifth embodiment.

As shown in FIG. 9, the probe 123 includes a pipe 132 including a screw portion 133 on the proximal end. A through hole 134 is formed in a coaxial center of the pipe 132 and screw portion 133. The distal end of a horn 171 of the grasp portion 122 described later is screwed/fastened and detachably attached to the proximal end of the probe 123 via the screw portion 133.

The grasp portion 122 includes a cylindrical outer portion 135. A flange portion 135a projecting in a central axis direction of the outer portion 135 is disposed on the distal end of the outer portion 135. A male screw portion 135b is formed on the outer peripheral surface of the distal end of the outer portion 135. A substantially cylindrical outer case 137 including a female screw portion 137a on the inner peripheral surface of the proximal end is screwed onto the male screw portion 135b. The outer peripheral surface of the outer portion 135 is on the same plane as that of the outer peripheral surface of the outer case 137. A flange portion 137b projecting toward the central axis direction of the outer case 137 is disposed on the distal end of the outer case 137. One end of a screw 180 described later is disposed on the flange portion 137b.

On the other hand, a female screw portion 135c is formed on the inner peripheral surface of the rear end of the outer portion 135. A substantially cylindrical outer case 141 including a male screw portion 141a on the outer peripheral surface of the distal end is screwed onto the female screw portion 135c. The inner peripheral surface of the outer portion 135 is on the same plane as that of the outer peripheral surface of the outer case 141.

In the outer case 141 of the rear end of the outer portion 135, a cap 143, a support portion 144, a hole for lead 145 of a lead wire 166 described later, and a hole for lead 146 of a lead wire 148a described later are integrally disposed.

The cap 143 is formed in a cylindrical shape, and disposed on the central axis of the outer portion 135 and outer case 141. One end of the suction tube 114 is connected to the proximal end of the cap 143. The other end of the suction tube 114 is connected to the suction pump 116a. An O ring 174 described later is disposed on the inner peripheral surface of the distal end of the cap 143 (inside the outer portion 135) to achieve the watertightness with a cylindrical bolt portion 172 described later.

The support portion 144 is formed in the cylindrical shape, and is disposed on the central axis of the outer portion 135 and outer case 141. The distal end of the support portion 144 abuts on the flange portion 135a of the distal end of the outer portion 135. At this time, a coil 148 which is the mechanical shock generation source and a metal coat film 149 are disposed in a space between the support portion 144 and the inner peripheral surface of the outer portion 135. The outer peripheral surface of the support portion 144 is coated with the metal coat film 149. That is, the coil 148 and metal coat film 149 are supported on the outer periphery of the support portion 144. The coil 148 and metal coat film 149 are attached to one end of the lead wire 148a whose other end is connected to the power supply main body 116 (see FIG. 8), and the wire extends rearwards.

A Langevin type ultrasonic vibrator 150 is contained as the ultrasonic vibration source inside the support portion 144. The outer peripheral surface of the ultrasonic vibrator 150 is disposed apart from the inner peripheral surface of the support portion 144.

The ultrasonic vibrator 150 includes a piezoelectric device 152, first and second electrode plates 154, 156, and metal blocks 158, 160.

The piezoelectric device 152, first electrode plate 154, and metal blocks 158, 160 are formed in annular shapes. The second electrode plate 156 is formed as a cylindrical bolt. A device support portion 156a for supporting the piezoelectric device 152 is disposed on the proximal end of the second electrode plate 156. The second electrode plate 156 is passed through the inner hole of the piezoelectric device 152, first electrode plate 154, and metal blocks 158, 160. Furthermore, a male screw portion 156b is disposed on the distal end of the second electrode plate 156. The male screw portion 156b is screwed onto a female screw portion 158a of the metal block 158. Furthermore, the second electrode plate 156 includes disc-shaped protrusions disposed every other piezoelectric device 152.

A plurality of piezoelectric devices 152 are disposed on the rear end of the front-side metal block 158. The first and second electrode plates 154, 156 are alternately disposed between the piezoelectric devices 152. The piezoelectric device 152 disposed on a rearmost side abuts on the device support portion 156a of the rear end of the second electrode plate 156. The device support portion 156a abuts on the rear-side metal block 160.

As described above, since the female screw portion 158a of the metal block 158 is screwed onto the male screw portion 156b of the second electrode plate 156, the piezoelectric device 152 is firmly held between the front-side metal block 158 and the device support portion 156a.

A male screw portion 160a screwed onto a female screw portion 141b of the inner peripheral surface of the outer case 141 is disposed on the outer peripheral surface of the rear-side metal block 160. Therefore, the Langevin type ultrasonic vibrator 150 is held in the outer case 141. It is to be noted that the electrode plates 154, 156 are connected to one end of the lead wire 166 whose other end is connected to the power supply main body 116 (see FIG. 8) and which extends rearwards.

A substantially conical oscillation section 170 is disposed on the distal end of the ultrasonic vibrator 150. That is, the oscillation section 170 abuts on the distal end of the metal block 158. The oscillation section 170 includes the horn 171 and bolt portion 172.

The horn 171 is formed substantially in the conical shape including an opening along the central axis. The screw portion 133 onto which the proximal end of the pipe 132 of the probe 123 is screwed is disposed on the distal end of the horn 171. A female screw portion 171a is formed on the proximal end of the horn 171.

The bolt portion 172 has a cylindrical shape and includes a male screw portion 172a on the outer peripheral surface of the distal end. The male screw portion 172a of the bolt portion 172 is screwed onto the female screw portion 171a of the proximal end of the horn 171 in a passed state inside the second electrode plate 156 (ultrasonic vibrator 150). On the other hand, the O ring 174 is disposed on the outer peripheral surface of the proximal end of the bolt portion 172 between the bolt portion and the inner peripheral surface of the cap 143. Therefore, the solution or the crushed solid matter is prevented from entering the ultrasonic vibrator 150, metal block 160 here, and the block is supported in a watertight manner.

A flange portion 175 projecting outwards in the diametric direction is integrally formed on the proximal end of the horn 171. An O ring receiving portion 177 in which an O ring 176 is disposed is disposed in the outer peripheral surface of the flange portion 175. The O ring 176 abuts on the inner peripheral surface of the outer case 137 on the distal end side. For example, a spring 180 is disposed as an elastic material which urges the flange portion 175 on the rear side of the outer case 137 between the flange portion 175 and the flange portion 137b of the outer case 137. One end of the spring 180 is supported by the flange portion 137b of the outer case 137 as described above. The other end of the spring 180 is supported by the flange portion 175. Therefore, the oscillation section 170 is slidable along a slide surface 137c which is the inner peripheral surface of the outer case 137 against the urging force of the spring 180 along the axial direction of the probe 123 in the outer case 137. The shock transmitted to both the horn 171 and the outer case 137 is absorbed by the O ring 176 and spring 180.

An annular permanent magnet 182 is disposed between the flange portion 175 and the flange portion 135a projecting in the central axis direction of the outer portion 135. The flange portion 175 abuts on the permanent magnet 182 from the rear end. For the permanent magnet 182, the flange portion 175 of the oscillation section 170 is urged rearwards by the spring 180. Therefore, the permanent magnet 182 is held between the flange portion 175 and the distal end of the outer portion 135.

The permanent magnet 182, and the coil 148 and metal coat film 149 magnetized at the time of the supply of the current function as the adjustment mechanism capable of adjusting the attached/detached state including an abutment (closely attached) state in which the oscillation section 170 is attracted by the Langevin type ultrasonic vibrator 150 that is the ultrasonic vibration source, and a repelled and detached state. The coil 148 and metal coat film 149 repeat the state in which the magnets are attracted by each other to abut on each other and the repelled and detached state by continuous switch of the direction of the current passed through the coil 148 and metal coat film 149, and therefore functions as the mechanical shock generation source.

Therefore, when a flow direction of the current passed through the coil 148 and metal coat film 149 from the power supply main body 116 is set, the ultrasonic vibration and mechanical shock force transmitted to the probe 123 are switched, and therefore the power supply main body 116 functions as the switch mechanism of the force transmitted to the probe 123.

The lead wire 166 is connected to the electrode plates 154, 156 and guided outside the lithotripsy probe apparatus 112 via the hole for lead 145. The lead wire 148a is connected to the coil 148 and guided outside the lithotripsy probe apparatus 112 via the hole for lead 146. The holes for lead 145, 146 are disposed adjacent to each other. In the hole for lead 146, a break preventive member 185 is disposed to cover the lead wire 148a electrically connected to the coil 148 and the lead wire 166 connected to the electrode plate 154 and to prevent disconnection.

Next, the method of using the lithotripsy system 110 will be described as the function of the lithotripsy system 110 with reference to FIGS. 8 and 9.

The probe 123 is fastened to the distal end of the oscillation section 170 of the grasp portion 122 using the screw portion 133 to form the lithotripsy probe apparatus 112. The connection portion 124a of the lithotripsy probe apparatus 112 is connected to the power supply main body 116. One end of the suction tube 114 is pressed into the cap for suction 143, and the other end of the tube is meshed with the suction pump 116a and guided into an excrement container (not shown). The power supply main body 116 is turned on to set the power supply main body 116 with the operation panel 116c. Switches (not shown) are operated to start output.

The power is supplied to the lithotripsy probe apparatus 112 from the power supply main body 116 through the connection portion 124a and power supply cord 124 in accordance with the setting of the operation panel 116c. The break preventive member 185 prevents the disconnection by the two-core lead wires 166, 148a in the power supply cord 124, and the power is transmitted to the inside of the grasp portion 122 through the holes for lead 145, 146. The setting of the operation panel 116c has specifications in which a mechanical vibration generation state and ultrasonic vibration generation state are selectable. First, the ultrasonic vibration generation state will be described.

The current is passed through the coil 148 and metal coat film 149 from the power supply main body 116 set to the ultrasonic vibration generation state via the lead wire 148a. The coil 148 and metal coat film 149 change the magnetic field and transforms the coil 148 into an electromagnet. The permanent magnet 182 and coil 148 attract each other. Therefore, the closely attached state is obtained in which the horn 171 of the oscillation section 170 is firmly pressed onto the metal block 158, that is, Langevin type ultrasonic vibrator 150.

On the other hand, the current is passed through the electrode plate 154 via the lead wire 166. This forms an electromotive force to vibrate the piezoelectric device 152. The ultrasonic vibration is generated in the piezoelectric device 152, the vibration is transmitted to the oscillation section 170 firmly pressed through the metal block 158, the amplitude is enlarged by the horn 171, and the ultrasonic vibration is transmitted to the distal end of the probe 123 through the screw portion 133 and pipe 132. The solid matters such as the calculus in the body cavity is crushed/treated by this ultrasonic vibration.

Next, the mechanical vibration generation state will be described. The ultrasonic vibration generation state of the power supply main body 116 is switched so as to set the mechanical vibration generation state. The current is passed through the coil 148 and metal coat film 149 via the lead wire 148a from the power supply main body 116 set to the mechanical vibration generation state. The magnetic field changes by the coil 148 and metal coat film 149, and the coil 148 is transformed into the electromagnet.

Here, for the current passed through the two-core lead wire 148a, the current is stopped in a pulse manner, or the flow direction of the current is reversed. Accordingly, the repelled and detached state with respect to the permanent magnet 182, and the state (or the attracted abutment state) in which the magnetic force is not produced are repeatedly generated. In a state in which the magnetic force is exerted in a repelling direction, the oscillation section 170 slides forwards along the outer case 137, and projects with a great force with respect to the grasp portion 122. At the next moment, the current direction is reversed, and the magnetic force is exerted in an attracted state. Or, the current is stopped to the coil 148, and the coil 148 is not-magnetized state. The urging the flange portion 175 of the spring 180 rearwards is used to return the oscillation section 170 to the grasp portion 122. This is continuously generated to realize the mechanical vibration generation state. The solid matters such as the calculus in the body cavity are broken/treated by this mechanical vibration.

Residues generated as a result of the lithotripsy treatment of the solid matters such as the calculus performed using the mechanical or ultrasonic vibration are discharged through the through hole 134 formed by the pipe 132, horn 171, bolt portion 172, and cap 143 via the suction tube 114 by the operation of the suction pump 116a of the power supply main body 116. It is to be noted that this discharge may be performed while generating the mechanical or ultrasonic vibration.

As described above, the lithotripsy system 110 according to the present embodiment obtains the following effect.

The breaking by the mechanical vibration (mechanical shock force) and the crushing by the ultrasonic vibration can easily be switched by the current passed from the power supply main body 116 to efficiently use both, and it is possible to crush/suck/remove the calculus. When the equivalent operation is performed in the related art, two lithotripsy treatment apparatuses have heretofore been required, but in the present invention, the operation can be done with one apparatus, and therefore a replacing operation during the operation is not required. Therefore, operability can be enhanced, and a surgical operation time can be reduced.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscopic lithotripsy apparatus comprising:
   an elongated probe which includes a distal end and a proximal end, the distal end being operable to be inserted into a body cavity;
   an ultrasonic vibration source detachably attached to the proximal end of the probe to transmit an ultrasonic vibration to the probe in a state in which the proximal end of the probe is connected to the ultrasonic vibration source;
   a mechanical shock generation source which is disposed on a side of the proximal end of the probe and which applies a force to the ultrasonic vibration source, in a state in which the ultrasonic vibration source is detached from the proximal end of the probe and which allows the ultrasonic vibration source to collide with the proximal end of the probe to apply a mechanical shock to the probe; and
   a switch mechanism to switch a state in which the ultrasonic vibration from the ultrasonic vibration source is transmitted to the proximal end of the probe and a state in which the mechanical shock from the mechanical shock generation source is transmitted, the switch mechanism including
      a cylindrical case in which the mechanical shock generation source is disposed in a cylindrical shape and in which the ultrasonic vibration source is disposed inside the mechanical shock generation source and which movably supports the ultrasonic vibration source with respect to the mechanical shock generation source and which includes a screw portion on the outer peripheral surface of the distal end;
      a coupling member which is supported by the inner peripheral surface of the distal end of the case and which is connected to the proximal end of the probe; and
      a cover member which includes a screw portion screwed onto the screw portion of the distal end of the case and which abuts on the coupling member and which is rotated by the distal end of the case so as to attach/detach the coupling member with respect to the ultrasonic vibration source.

2. The endoscopic lithotripsy apparatus according to claim 1, wherein the mechanical shock generation source includes a coil which is disposed on an outer periphery of the ultrasonic vibration source and which generates a magnetic force to move the ultrasonic vibration source toward the proximal end of the probe, when a pulse current is supplied to the coil.

3. The endoscopic lithotripsy apparatus according to claim 2, wherein the ultrasonic vibration source includes a Langevin type ultrasonic vibrator to ultrasonically vibrate when a power is supplied to the ultrasonic vibrator, and a horn which is connected to the ultrasonic vibrator to enlarge an amplitude of the ultrasonic vibration generated by the ultrasonic vibrator.

4. The endoscopic lithotripsy apparatus according to claim 3, wherein the probe and the ultrasonic is vibrator are formed on the same axis and have cylindrical shapes in which communication holes communicating with each other are formed, and the ultrasonic vibration source includes a suction device connected to the proximal end of the ultrasonic vibration source so as to be capable of automatically sucking a crushed treatment object through the communication hole in a state in which the ultrasonic vibration is transmitted to the proximal end of the probe from the ultrasonic vibration source.

5. The endoscopic lithotripsy apparatus according to claim 4, wherein the suction device includes a suction switch connected to the suction device so as to forcibly operate the suction device.

6. The endoscopic lithotripsy apparatus according to claim 1, wherein the mechanical shock generation source includes a coil which is disposed on an outer periphery of the ultrasonic vibration source to generate a magnetic force to move the ultrasonic vibration source toward the proximal end of the probe, when a pulse current is supplied to the coil.

7. The endoscopic lithotripsy apparatus according to claim 6, wherein the ultrasonic vibration source includes a Langevin type ultrasonic vibrator to ultrasonically vibrate when a power is supplied to the ultrasonic vibrator, and a horn which is connected to the ultrasonic vibrator to enlarge an amplitude of the ultrasonic vibration generated by the ultrasonic vibrator.

8. The endoscopic lithotripsy apparatus according to claim 1, wherein the probe and the ultrasonic vibrator are formed on the same axis and have cylindrical shapes in which communication holes communicating with each other are formed, and the ultrasonic vibration source includes a suction device connected to the proximal end of the ultrasonic vibration source so as to be capable of automatically sucking a crushed treatment object through the communication hole in a state in which the ultrasonic vibration is transmitted to the proximal end of the probe from the ultrasonic vibration source 9. The endoscopic lithotripsy apparatus according to claim 1, wherein the ultrasonic vibration source includes a Langevin type ultrasonic vibrator to ultrasonically vibrate when a power is supplied to the ultrasonic vibrator, and a horn which is connected to the ultrasonic vibrator to enlarge an amplitude of the ultrasonic vibration generated by the ultrasonic vibrator.

10. An endoscopic lithotripsy apparatus comprising:
an elongated probe which includes a distal end and a proximal end, the distal end being to be inserted into a body cavity;
an ultrasonic vibration source detachably attached to the proximal end of the probe to transmit an ultrasonic vibration to the probe in a connected state to the proximal end of the probe;
a mechanical shock generation source which is disposed on a side of the proximal end of the probe and which applies a force in a direction to detach the proximal end of the probe with respect to the ultrasonic vibration source to apply a mechanical shock to a treatment object from the distal end of the probe;
a switch mechanism to switch a state in which the ultrasonic vibration from the ultrasonic vibration source is transmitted to the proximal end of the probe and a state in which the mechanical shock from the mechanical shock generation source is transmitted, and
the switch mechanism including:
a cylindrical case in which the mechanical shock generation source is disposed in a cylindrical shape and in which the ultrasonic vibration source is disposed inside the mechanical shock generation source and which movably supports the ultrasonic vibration source with respect to the mechanical shock generation source and which includes a screw portion on the outer peripheral surface of the distal end;
a coupling member which is supported by the inner peripheral surface of the distal end of the case and which is connected to the proximal end of the probe; and
a cover member which includes a screw portion screwed onto the screw portion of the distal end of the case and which abuts on the coupling member and which is rotated by the distal end of the case so as to attach/detach the coupling member with respect to the ultrasonic vibration source.

11. The endoscopic lithotripsy apparatus according to claim 10, wherein the mechanical shock generation source includes a coil which generates a magnetic force to move the probe in the axial direction, when a pulse current is supplied to the coil.

12. The endoscopic lithotripsy apparatus according to claim 11, wherein the ultrasonic vibration source includes a Langevin type ultrasonic vibrator to ultrasonically vibrate when a power is supplied to the ultrasonic vibrator, and a horn which is connected to the ultrasonic vibrator to enlarge an amplitude of the ultrasonic vibration generated by the ultrasonic vibrator.

13. The endoscopic lithotripsy apparatus according to claim 12, wherein the probe and the ultrasonic vibration source are formed on the same axis and have cylindrical shapes in which communication holes communicating with each other are formed, and the ultrasonic vibration source includes a suction device connected to the proximal end of the ultrasonic vibration source so as to be capable of automatically sucking a crushed treatment object through the communication hole in a state in which the ultrasonic vibration is transmitted to the proximal end of the probe from the ultrasonic vibration source.

14. The endoscopic lithotripsy apparatus according to claim 13, wherein the suction device includes a suction switch connected to the suction device so as to forcibly operate the suction device.

15. The endoscopic lithotripsy apparatus according to claim 13, wherein the switch mechanism includes an engaging portion which detachably attaches the proximal end of the probe to the ultrasonic vibration source.

16. The endoscopic lithotripsy apparatus according to claim 15, wherein the engaging portion includes a screw portion.

17. The endoscopic lithotripsy apparatus according to claim 16, wherein the probe includes a handle which adjusts a closely attached state between the proximal end of the probe and the ultrasonic vibration source.

18. The endoscopic lithotripsy apparatus according to claim 17, wherein the mechanical shock generation source includes a coil which generates a magnetic force to move the probe in the axial direction, when a pulse current is supplied to the coil.

19. The endoscopic lithotripsy apparatus according to claim 17, wherein the ultrasonic vibration source includes a Langevin type ultrasonic vibrator to ultrasonically vibrate when a power is supplied to the ultrasonic vibrator, and a horn which is connected to the ultrasonic vibrator to enlarge an amplitude of the ultrasonic vibration generated by the ultrasonic vibrator.

20. The endoscopic lithotripsy apparatus according to claim 17, wherein the probe and the ultrasonic vibration source are formed on the same axis and have cylindrical shapes in which communication holes communicating with each other are formed, and the ultrasonic vibration source includes a suction device connected to the proximal end of the ultrasonic vibration source so as to be capable of automatically sucking a crushed treatment object through the communication hole in a state in which the ultrasonic vibration is transmitted to the proximal end of the probe from the ultrasonic vibration source.

21. The endoscopic lithotripsy apparatus according to claim 14, wherein the switch mechanism includes the mechanical shock generation source in a cylindrical shape, the ultrasonic vibration source is disposed inside the mechanical shock generation source, and the switch mechanism includes an engaging portion to switch a state in which the ultrasonic vibration source is fixed to the mechanical shock generation source and a state in which the ultrasonic vibration source is movable with respect to the mechanical shock generation source.

22. The endoscopic lithotripsy apparatus according to claim 21, wherein the engaging portion is disposed on the inner peripheral surface of the mechanical shock generation source and on the outer peripheral surface of the ultrasonic vibration source.

23. The endoscopic lithotripsy apparatus according to claim 21, wherein the mechanical shock generation source includes a coil to generate a magnetic force to move the probe along the axial direction, when a pulse current is supplied to the coil.

24. The endoscopic lithotripsy apparatus according to claim 21, wherein the ultrasonic vibration source includes a Langevin type ultrasonic vibrator to ultrasonically vibrate when a power is supplied to the ultrasonic vibrator, and a horn which is connected to the ultrasonic vibrator to enlarge an amplitude of the ultrasonic vibration generated by the ultrasonic vibrator.

25. The endoscopic lithotripsy apparatus according to claim 21, wherein the probe and the ultrasonic vibration source are formed on the same axis and have cylindrical shapes in which communication holes communicating with each other are formed, and the ultrasonic vibration source includes a suction device connected to the proximal end of the ultrasonic vibration source so as to be capable of automatically sucking a crushed treatment object through the communication hole in a state in which the ultrasonic vibration is transmitted to the proximal end of the probe from the ultrasonic vibration source.

26. The endoscopic lithotripsy apparatus according to claim 14, wherein the mechanical shock generation source includes a coil which is disposed on an outer periphery of the ultrasonic vibration source to generate a magnetic force to move the probe along the axial direction, when a pulse current is supplied to the coil, and the switch mechanism includes a permanent magnet attached/detached with respect to the proximal end of the probe by the direction of the magnetic force generated based on the direction of the current passed through the coil.

27. The endoscopic lithotripsy apparatus according to claim 26, wherein the ultrasonic vibration source includes a Langevin type ultrasonic vibrator to ultrasonically vibrate when a power is supplied to the ultrasonic vibrator, and a horn which is connected to the ultrasonic vibrator to enlarge an amplitude of the ultrasonic vibration generated by the ultrasonic vibrator.

28. The endoscopic lithotripsy apparatus according to claim 26, wherein the probe and the ultrasonic vibration source are formed on the same axis and have cylindrical shapes in which communication holes communicating with each other are formed, and the ultrasonic vibration source includes a suction device connected to the proximal end of the ultrasonic vibration source so as to be capable of automatically sucking a crushed treatment object through the communication hole in a state in which the ultrasonic vibration is transmitted to the proximal end of the probe from the ultrasonic vibration source.

29. The endoscopic lithotripsy apparatus according to claim 10, wherein the probe and the ultrasonic vibration source are formed on the same axis and have cylindrical shapes in which communication holes communicating with each other are formed, and the ultrasonic vibration source includes a suction device connected to the proximal end of the ultrasonic vibration source so as to be capable of automatically sucking a crushed treatment object through the communication hole in a state in which the ultrasonic vibration is transmitted to the proximal end of the probe from the ultrasonic vibration source.

30. The endoscopic lithotripsy apparatus according to claim 10, wherein the ultrasonic vibration source includes a Langevin type ultrasonic vibrator to ultrasonically vibrate when a power is supplied to the ultrasonic vibrator, and a horn which is connected to the ultrasonic vibrator to enlarge an amplitude of the ultrasonic vibration generated by the ultrasonic vibrator.

31. A lithotripsy method for a treatment object comprising:
  providing an endoscopic lithotripsy apparatus comprising:
    an elongated probe which includes a distal end and a proximal end; and a switch mechanism including a cylindrical case in which the mechanical shock generation source is disposed in a cylindrical shape and in which the ultrasonic vibration source is disposed inside the mechanical shock generation source and which movably supports the ultrasonic vibration source with respect to the mechanical shock generation source and which includes a screw portion on the outer peripheral surface of the distal end; a coupling member which is supported by the inner peripheral surface of the distal end of the case and which is connected to the proximal end of the probe; and a cover member which includes a screw portion screwed onto the screw portion of the distal end of the case and which abuts on the coupling member and which is rotated by the distal end of the case so as to attach/detach the coupling member with respect to the ultrasonic vibration source;
  inserting the elongated probe of the endoscopic lithotripsy apparatus including the probe into a body cavity;
  supplying a power to the mechanical shock generation source and applying a mechanical shock to a proximal end of the probe inserted in the body cavity to crush the treatment object by the distal end of the probe;
  connecting the ultrasonic vibration source to the proximal end of the probe to supply the power to the ultrasonic vibration source; transmitting an ultrasonic vibration to the proximal end of the probe to further finely crush the treatment object by the distal end of the probe; and
  using the switch mechanism to switch between applying the mechanical shock with the mechanical shock generation source and connecting the ultrasonic vibration source to the proximal end of the probe.

32. The lithotripsy method of the treatment object using the endoscopic lithotripsy apparatus according to claim 31, further comprising:
  connecting the ultrasonic vibration source to the proximal end of the probe to supply the power to the ultrasonic vibration source and transmitting the ultrasonic vibration to the proximal end of the probe to finely crush the treatment object by the distal end of the probe and to suck the crushed treatment object.

33. A lithotripsy method of a treatment object using an endoscopic lithotripsy apparatus, comprising:
  providing an endoscopic lithotripsy apparatus comprising:
    an elongated probe which includes a distal end and a proximal end; and a switch mechanism including a cylindrical case in which the mechanical shock generation source is disposed in a cylindrical shape and in which the ultrasonic vibration source is disposed inside the mechanical shock generation source and which movably supports the ultrasonic vibration source with respect to the mechanical shock generation source and which includes a screw portion on the outer peripheral surface of the distal end; a coupling member which is supported by the inner peripheral surface of the distal end of the case and which is connected to the proximal end of the probe; and a cover member which includes a screw portion screwed onto the screw portion of the distal end of the case and which abuts on the coupling member and which is rotated by the distal end of the case so as to attach/detach the coupling member with respect to the ultrasonic vibration source;
  inserting the elongated probe of the endoscopic lithotripsy apparatus including the probe into a body cavity;
  supplying a power to the mechanical shock generation source and moving the probe inserted in the body cavity in an axial direction of the probe to crush the treatment object by the distal end of the probe;
  closely attaching the ultrasonic vibration source to the proximal end of the probe to supply the power to the ultrasonic vibration source;
  and transmitting an ultrasonic vibration to the proximal end of the probe to further finely crush the treatment object by the distal end of the probe.

* * * * *

UNITED STATES PATENT AND TRADEMARK OFFICE
CERTIFICATE OF CORRECTION

PATENT NO. : 7,645,245 B2
APPLICATION NO. : 10/729074
DATED : January 12, 2010
INVENTOR(S) : Sekino et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1713 days.

Signed and Sealed this

Sixteenth Day of November, 2010

David J. Kappos
*Director of the United States Patent and Trademark Office*